(12) United States Patent
Li et al.

(10) Patent No.: US 9,958,453 B2
(45) Date of Patent: May 1, 2018

(54) BIOLOGICAL SENSING METHOD FOR SEPARATING BIOMOLECULE

(71) Applicant: NATIONAL CHIAO TUNG UNIVERSITY, Hsinchu (TW)

(72) Inventors: Yaw-Kuen Li, Hsinchu (TW); Chia-Yu Chang, Taipei (TW); Bor-Ran Li, Hsinchu (TW)

(73) Assignee: NATIONAL CHIAO TUNG UNIVERSITY, Hsinchu (TW)

( * ) Notice: Subject to any disclaimer, the term of this patent is extended or adjusted under 35 U.S.C. 154(b) by 6 days.

(21) Appl. No.: 15/229,111

(22) Filed: Aug. 5, 2016

(65) Prior Publication Data

US 2016/0341738 A1    Nov. 24, 2016

Related U.S. Application Data

(62) Division of application No. 14/740,269, filed on Jun. 16, 2015.

(30) Foreign Application Priority Data

Mar. 10, 2015  (TW) .............................. 104107616 A

(51) Int. Cl.
*G01N 33/68* (2006.01)
*G01N 33/569* (2006.01)
*G01N 1/40* (2006.01)
*G01N 27/414* (2006.01)

(52) U.S. Cl.
CPC ............ *G01N 33/68* (2013.01); *G01N 1/405* (2013.01); *G01N 27/4145* (2013.01); *G01N 33/56944* (2013.01); *G01N 33/6878* (2013.01); *G01N 2333/3156* (2013.01)

(58) Field of Classification Search
CPC ................................................. G01N 33/6878
See application file for complete search history.

(56) References Cited

U.S. PATENT DOCUMENTS

| | | | |
|---|---|---|---|
| 7,718,375 B2 | 5/2010 | Piasio et al. | |
| 8,043,812 B2 | 10/2011 | Seki et al. | |
| 2005/0203280 A1 | 9/2005 | McMichael et al. | |
| 2008/0241191 A1 | 10/2008 | Moore et al. | |
| 2013/0052641 A1 | 2/2013 | Garcia Lopez et al. | |

FOREIGN PATENT DOCUMENTS

| CN | 1670204 A | 9/2005 |
|---|---|---|
| TW | I231299 B | 4/2005 |

OTHER PUBLICATIONS

Navarro et al., "Performance of the Binax now *Streptococcus pneumoniae* Urinary Antigen Assay for Diagnosis of Pneumonia in Children with Underlying Pulmonary Diseases in the Absence of Acute Pneumococcal Infection", Journal of Clinical Microbiology, vol. 42, pp. 4853-4855, 2004.

Fernando et al., "Molecular Architecture of the Mn2+-dependent Lactonase UlaG Reveals an RNase-like Metallo-β-lactamase Fold and a Novel Quaternary Structure", Journal of Molecular Biology, vol. 398, pp. 715-729, 2010.

Beghetto et al., "Discovery of novel *Streptococcus pneumoniae* antigens by screening a whole-genome lambda-display library", FEMS Microbiology Letters, vol. 262, pp. 14-21, 2006.

Morozumi et al., "Simultaneous Detection of Pathogens in Clinical Samples from Patients with Community-Acquired Pneumonia by Real-Time PCR with Pathogen-Specific Molecular Beacon Probes", Journal of Clinical Microbiology, vol. 44, pp. 1440-1446, 2006.

Carvalho et al., "Evaluation and Improvement of Real-Time PCR Assays Targeting lytA, ply, and psaA Genes for Detection of Pneumococcal DNA", Journal of Clinical Microbiology, vol. 45, pp. 2460-2466, 2007.

Fernandez et al., "The UlaG protein family defines novel structural and functional motifs grafted on an ancient RNase fold.", BMC Evolutionary Biology 2011, 11:273.

Evangelina Campos et al., "Regulation of Expression of the Divergent ulaG and ulaABCDEF Operons Involved in L-Ascorbate Dissimilation in *Escherichia coli*.", Journey of Bacteriology, Mar. 2004, vol. 186, No. 6., pp. 1720-1728.

Fernando Garces et al., "Overproduction, crystallization and preliminary X-ray analysis of the putative L-ascorbate-6-phosphate lactonase UlaG from *Escherichia coli*.", Acta Crystallographica Section F Structural Biology and Crystallization Communications, (2008) F64, pp. 36-38.

*Primary Examiner* — Bin Shen
(74) *Attorney, Agent, or Firm* — CKC & Partners Co., Ltd.

(57) ABSTRACT

A biological sensing device and a method for separating a biomolecule are provided. The biological sensing device includes an amino acid sequence and a signal-generating unit. The amino acid sequence includes SEQ ID NO: 1 or SEQ ID NO: 2, and is for binding with UlaG protein labeled on a biomolecule. The signal-generating unit connects to the amino acid sequence.

4 Claims, 4 Drawing Sheets

BIOLOGICAL SENSING METHOD FOR SEPARATING BIOMOLECULE

RELATED APPLICATIONS

The present application is a Divisional Application of the U.S. application Ser. No. 14/740,269, filed Jun. 16, 2015, which claims priority to Taiwan Application Serial Number 104107616, filed Mar. 10, 2015, all of which are, herein incorporated by reference.

SEQUENCE LISTING

The sequence listing submitted via EFS, in compliance with 37 CFR § 1.52(e)(5), is incorporated herein by reference. The sequence listing text file submitted via EFS contains the file "Biological sensing device and method for separating biomolecule-sequencelisting", created on Aug. 1, 2016, which is 602 bytes in size.

BACKGROUND

Field of Invention

The present invention relates to a biological sensing device and a method for separating a biomolecule. More particularly, the present invention relates to a biological sensing device and a method for separating a biomolecule using an amino acid sequence.

Description of Related Art

Biological sensing technology measures the response of organism or biological material to external stimulation, which has a wide range of applications, and can promote the development of pharmaceuticals, biomedical detection, environmental engineering, food analysis, and biotechnology. However, most of current biological sensing technology use polyclonal antibodies with high uncertainty or monoclonal antibodies with high cost to detect the sample to be analyzed. The detecting result has poor sensitivity, and is prone to misdiagnosis.

Accordingly, there is a need for biological sensing device and a method for separating a biomolecule, which have advantages of being rapid, accurate, and low cost.

SUMMARY

An aspect of the present invention provides a biological sensing device, including an amino acid sequence and a signal-generating unit. The amino acid sequence includes SEQ ID NO: 1 or SEQ ID NO: 2, and is for binding with UlaG protein labeled on a biomolecule. The signal-generating unit connects to the amino acid sequence.

According to an embodiment of the present invention, the biomolecule is a protein, a cell, a bacterium, or a combination thereof.

According to an embodiment of the present invention, the bacterium is a Gram-positive bacterium.

According to an embodiment of the present invention, the Gram-positive bacterium is from the genus *Streptococcus*.

According to an embodiment of the present invention, the Gram-positive bacterium from the genus *Streptococcus* is *Streptococcus pneumoniae*.

According to an embodiment of the present invention, the signal-generating unit is a transistor, a fluorescent molecule, or a chip.

Another aspect of the present invention provides a method for separating a biomolecule, including providing a sample, which the sample includes a biomolecule having UlaG protein. Next, the sample is contacted with an amino acid sequence including SEQ ID NO: 1 or SEQ ID NO: 2. The amino acid sequence binds with the UlaG protein. Then, a portion of the sample that is not bound with the amino acid sequence s removed to separate the biomolecule from the sample.

According to an embodiment of the present invention, the method for separating the biomolecule further includes modifying the UlaG protein onto the biomolecule.

According to an embodiment of the present invention, the method for separating the biomolecule further includes modifying the sample onto a substrate.

According to an embodiment of the present invention, the method for separating the biomolecule further includes connecting the amino acid sequence to a signal-generating unit.

The biological sensing device and the method for separating the biomolecule utilize the high affinity between the amino acid sequence and the UlaG protein to screen the biomolecule that is labeled with the UlaG protein. The purpose of the present invention is to provide a fast, accurate, and low-cost biological sensing device and method for separating a biomolecule.

BRIEF DESCRIPTION OF THE DRAWINGS

The invention can be more fully understood by reading the following detailed description of the embodiment, with reference made to the accompanying drawings as follows.

DETAILED DESCRIPTION

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples. Therefore, the spirit and scope of the appended claims should not be limited to the description of the embodiments contained herein.

Figure 1:
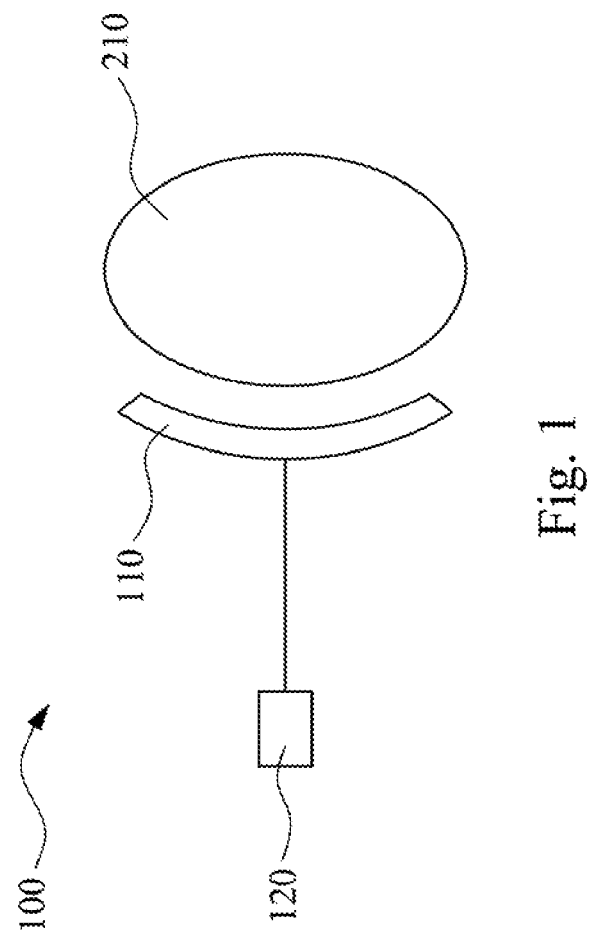
FIG. 1 is a schematic view of a biological sensing device according to an embodiment of the present invention bound with UlaG protein.

FIG. 1 is schematic view of a biological sensing device 100 according to an embodiment of the present invention bound with UlaG protein 210. The biological sensing device 100 includes an amino acid sequence 110 and a signal-generating unit 120. The UlaG protein 210 is labeled on a biomolecule (not shown). The amino acid sequence 110 includes the sequence shown in SEQ ID NO: 1 or SEQ ID NO: 2, and is for binding with the UlaG protein 210, which is labeled on the biomolecule. The signal-generating unit 120 connects to the amino acid sequence 110.

The UlaG protein 210 (L-ascorbate-6-phosphate lactonases) is a cell wall protein, and is commonly found in the cell wall of *Streptococcus*. The amino acid sequence 110 has high binding affinity to the UlaG protein, and therefore the biological sensing device 100 can recognize the biomolecule having the UlaG protein 210 through this binding relationship.

The biomolecule can be any substance that is desired to be detected. In an embodiment of the present invention, the biomolecule is a protein, a cell, a bacterium, or a combination thereof. In another embodiment of the present invention, the bacterium is a Gram-positive bacterium. The Gram-positive bacterium may be from the genus *Streptococcus*. In an embodiment of the present invention, the Gram-positive bacterium from the genus *Streptococcus* is *Streptococcus pneumoniae*.

In an embodiment of the present invention, the UlaG protein 210 is a surface protein of the biomolecule. In another embodiment of the present invention, the biomolecule is modified to be labeled with the UlaG protein 210. The biological sensing device 100 utilizes the binding between the amino acid sequence 110 and the UlaG protein 210 to recognize the biomolecule. Further, after the amino acid sequence 110 bound to the UlaG protein 210, the amount of the biomolecule and be analyzed by the signal generated by the signal-generating unit 120. For instance, the amount of the biomolecule labeled with the UlaG protein 210 can be determined by measuring the difference of the signals generated by the signal-generating unit 120 before and after the binding of the amino acid sequence 110 and the UlaG protein 210.

The amino acid 110 is used as a recognition factor for the UlaG protein 210, and a short sequence of 7 amino acids. Therefore, the amino acid 110 can be easily and largely obtained by chemical synthesis, and highly purified target protein can be obtained at a low cost.

The binding of the amino acid sequence 110 and the UlaG protein 210 would stimulate the signal-generating unit 120 to generate the signal. The signal-generating unit 120 may be a transistor, a fluorescent molecule, or a chip, and the signal generated by the signal-generating unit 120 may be a chrominance signal, fluorescent signal, or an electronic signal.

In an embodiment of the present invention, the biological sensing device further includes a fixing unit to connect the amino acid sequence to the signal-generating unit. The fixing unit may be a polyhistidine-tag (His-tag), a divalent ion, isothiocyanate nitrilotriacetic acid (NCS-NTA), (3-aminopropyl) trimethoxysilane (APTMS), or a combination thereof.

The biological sensing device 100 of the present invention applies the UlaG protein 210 to label the biomolecule, and separates the biomolecule through the binding of the amino acid sequence 110 and the UlaG protein 210. Further, due the biding of the amino acid sequence 110 and the UlaG protein 210, the signal-generating unit 120 would generate the signal. The amount of the biomolecule can be determined by the generated signal. The biological sensing device of the present invention can be combined with various existing detecting methods, such as fluorescent dye, quartz microbalance, and field effect transistor, and can be used in biomedical industry, such as clinical testing and home care.

Another aspect of the present invention provides a method for separating a biomolecule, including providing a sample, which the sample includes a biomolecule having UlaG protein. Next, the sample is contacted with an amino acid sequence including SEQ ID NO: 1 or SEQ ID NO: 2. The amino acid sequence binds with the UlaG protein. Then, a portion of the sample that is not bound with the amino acid sequence is removed to separate the biomolecule from the sample.

In an embodiment of the present invention, the UlaG protein is a surface protein of the biomolecule. In another embodiment of the present invention, the method for separating the biomolecule further includes modifying the UlaG protein onto the biomolecule to be detected. By contacting with the amino acid sequence, the biomolecule can be separated, and therefore the amount of the biomolecule in the sample can be analyzed.

In an embodiment of the present invention, the method for separating the biomolecule further includes modifying the sample onto a substrate before contacting the sample with the amino acid sequence. In this embodiment, the method for separating the biomolecule is to contact the amino acid sequence to the substrate modified with the sample, so that the amino acid sequence can react with and bind to the UlaG protein of the biomolecule in the sample, and thereby separating the biomolecule with the UlaG protein. The substrate can be a substrate commonly used for a biosensor, such as a silicon substrate, a glass substrate, and a metal substrate. In this embodiment, the amino acid sequence may be connected to a signal-generating unit, which the signal-generating unit may be a fluorescent molecule.

In an embodiment of the present invention, the method for separating the biomolecule further includes modifying the amino acid sequence onto a substrate before contacting the sample with the amino acid sequence. In this embodiment, the method for separating the biomolecule is to contact the sample to the substrate modified with the amino acid sequence, so that the UlaG protein of the biomolecule in the sample can react with and bind to the amino acid sequence, and thereby separating the biomolecule with the UlaG protein. The substrate may be a signal-generating unit, such as a field-effect transistor.

In an embodiment of the present invention, the method for separating the biomolecule further includes connecting the amino acid sequence to a signal-generating unit before contacting the sample with the amino acid sequence. After removing the portion in the sample that is not bound with the amino acid sequence to separate the biomolecule from the sample, the signal-generating unit would generate and emit a signal due to the binding of the amino acid sequence and the UlaG protein. The signal is used to detect the biomolecule with the UlaG protein in the sample and its amount. In some embodiment, the amino acid sequence is connected to the signal-generating unit through a fixing unit to fix the amino acid sequence and the signal-generating unit. The fixing unit may be a His-tag, a divalent ion, NCS-NTA, APTMS, or a combination thereof.

The method for separating the biomolecule of the present invention applies the UlaG protein to label the biomolecule, and separates the biomolecule with the UlaG protein, which is bound to the amino acid sequence, from the sample through the binding of the amino acid sequence and the UlaG protein. Therefore, the biomolecule and the amount thereof in the sample can be detected. The amount of the biomolecule may be determined by the signal generated by signal-generating unit, which is connected to the amino acid sequence. The method for separating the biomolecule of the present invention can be combined with various existing detecting methods, and can be used in biomedical industry, such as clinical testing and home care.

The detailed description provided below is intended as a description of the present examples and is not intended to represent the only forms in which the present example may be constructed or utilized. Therefore, the spirit and scope of the appended claims should not be limited to the description of the embodiments contained herein.

Screening of Amino Acid Sequence

The screening method of an amino acid according to an embodiment of the present invention included the following steps:

1. UlaG protein was largely expressed by *Escherichia coli*
2. The UlaG protein in step 1 was purified, and then modified onto an enzyme-linked immunosorbent assay (ELISA) plate.
3. Phage display peptide system was used to perform the screening. The phage display peptide system used bacteriophages with various peptide segments to contact the UlaG protein. After a process of repeated binding, washing, eluting, amplifying, and re-binding, the bacteriophage that can bind to the UlaG protein was selected.
4. The selected bacteriophage in step 3 was amplified and sequenced by polymerase chain reaction (PCR). The amino acid sequence that can bind to the UlaG protein was then obtained.

By using this screening method, both of the sequences shown in SEQ ID NO: 1 and SEQ ID NO: 2 can bind to the UlaG protein, and have high binding affinities to the UlaG protein. Therefore, an amino acid sequence including the sequence shown in SEQ ID NO: 1 or SEQ ID NO: 2 can be used in the recognition of the UlaG protein.

Detecting of *Streptococcus pneumoniae*

*Streptococcus pneumoniae* is the main cause of bacterial pneumonia. There are more than 400 millions infected with bacterial pneumonia worldwide each year, which causes more than one million deaths, and mostly are children. Therefore, the establishment of a rapid detecting technology of *Streptococcus pneumoniae* would contribute to rapid screening and subsequent treatment of *Streptococcus pneumoniae*, and could save millions of patients. However, the currently used detecting technology for *Streptococcus pneumoniae* has poor sensitivity, which is prone to misdiagnosis, or requires several days for bacterial culture. For instance, polymerase chain reaction (PCR) uses specific primers to perform chain reaction to the specimen to amplify the specific DNA sequences so as to determine whether the specimen includes *Streptococcus pneumoniae*-related sequences, and thereby determining whether the subject is infected with *Streptococcus pneumoniae*. The advantages of PCR is fast detection, while the disadvantage of which is that it is not highly sensitive. Besides, currently commercially available screening kit (BinaxNOW®) urine applies antigen testing technology, which uses immunochromatographic assay to detect whether the urine contains pneumococcal antigen of *Streptococcus pneumoniae* so as to determine whether the subject is infected with *Streptococcus pneumoniae*. The advantage of this kit is quick interpretation, while the disadvantage of which is that the urine antigen of *Streptococcus pneumoniae* can sustain for a month, and thus is prone to misdiagnosis. Therefore, currently, whether the subject is confirmed being infected with *Streptococcus pneumoniae*, antibiotics are usually administrated directly as the treatment in clinical. Such unconfirmed type of administration often results in waste of medical resources, damage to patient health, and increasing the risk of the evolution of multidrug-resistant bacteria.

UlaG protein is expressed in the cell wall of *Streptococcus pneumoniae*. The following experimental example used the biological sensing device of the present invention to detect whether the sample included *Streptococcus pneumoniae*, and the detecting method included the following steps:

1. The amino acid sequence including the sequence shown in SEQ ID NO: 1 was largely expressed by *Escherichia coli*.
2. The amino acid sequence in step 1 was purified, and then modified onto a surface of a field-effect transistor.
3. The field-effect transistor modified with the amino acid sequence in step 2 was contact to broths of *Streptococcus pneumoniae* with different concentrations, and the potential difference of the surface of the field-effect transistor modified was measured. The strain of *Streptococcus pneumoniae* used in this experimental example was ATCC 49136.

Figure 2:
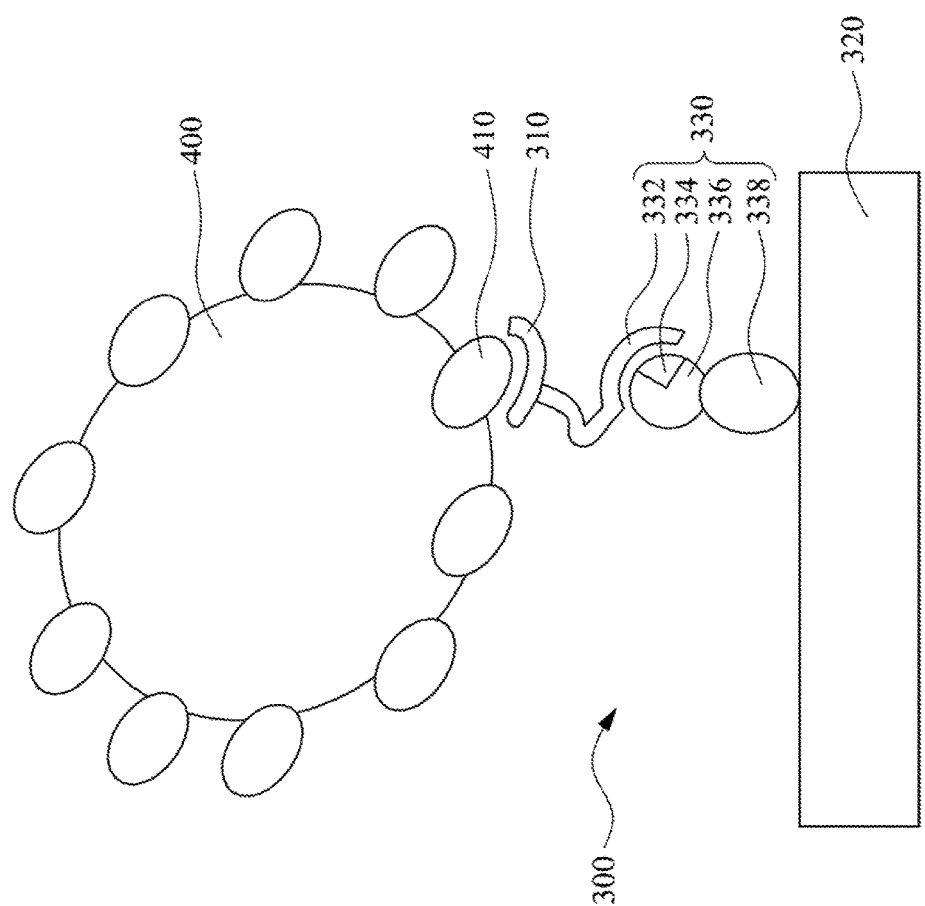
FIG. 2 is a schematic view of a biological sensing device according to an embodiment of the present invention detecting a biomolecule.

The biological sensing device used in the experimental example was as that shown in FIG. 2. FIG. 2 is a schematic view of a biological sensing device 300 according to an embodiment of the present invention detecting a biomolecule 400. The biological sensing device 300 includes an amino acid sequence 310, a signal-generating unit 320, and a fixing unit 330. The UlaG protein 410 is labeled on the biomolecule 400. The amino acid sequence 310 includes the sequence shown in SEQ ID NO: 1 or SEQ ID NO: 2, and is for binding with the UlaG protein 410, which is labeled on the biomolecule 400. The signal-generating unit 320 connects to the amino acid sequence 310 through the fixing unit 330. The fixing unit 330 includes a His-tag 332, a divalent ion 334, NCS-NTA 336, and APTMS 338. In this experimental example, the biomolecule 400 was *Streptococcus pneumoniae*. The signal-generating unit 320 was a field-effect transistor. The divalent ion 334 was nickel cation ($Ni^{2+}$). The His-tag 332 has high affinity to the divalent ion 334, and the divalent ion 334 forms a chelate with the NCS-NTA 336. The NCS-NTA 336 and the APTMS 338 are covalently bonded to be fixed to the signal-generating unit 320. The amino acid sequence 310 is fixed to the signal-generating unit 320 through connection of the His-tag 332, the divalent ion 334, the NCS-NTA 336, and the APTMS 338.

Figure 3:
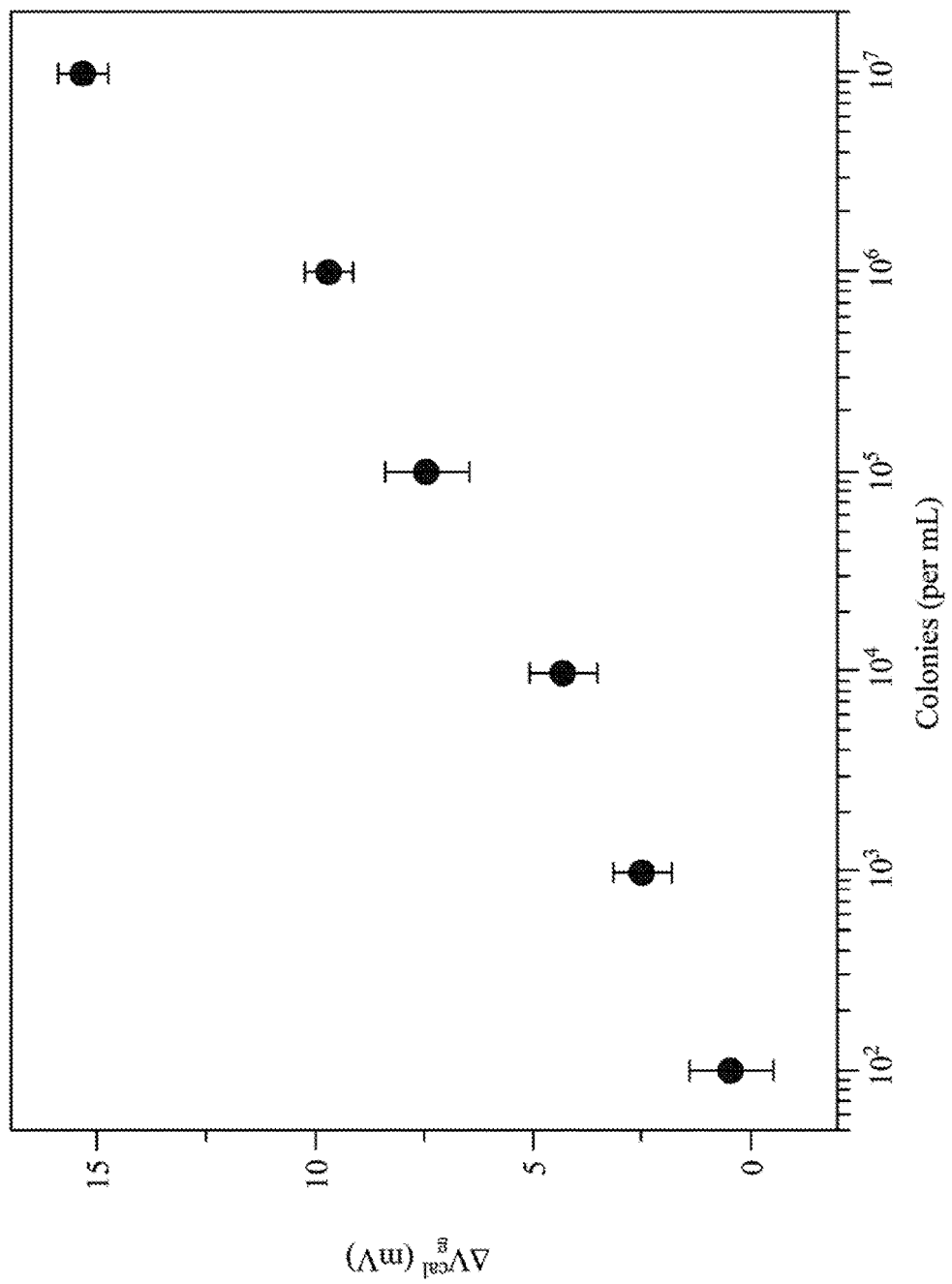
FIG. 3 is a potential difference-bacterial concentration diagram of an embodiment of the present invention for a detecting experiment.

FIG. 3 is a potential difference-bacterial concentration diagram of an embodiment of the present invention for the detecting experiment, which the bacterial concentration is represented by the number of colonies per milliliter (mL) of the broth. As shown, in FIG. 3, the potential difference increased with the increase of the bacterial concentration. This result suggests that the change in the surface potential of the biological sensing device of the present embodiment is positive correlated to the concentration of *Streptococcus pneumoniae*. The *Streptococcus pneumoniae* can be detected by the change in the surface potential.

Furthermore, the present experimental example applied *Streptococcus mutans* as a comparative example using the abovementioned biological sensing device 300 and detecting method. The field-effect transistor modified with the amino acid sequence including the sequence shown in SEC) ID NO: 1 was contact to broths of *Streptococcus mutans* with different concentrations, and the potential difference of the surface of the field-effect transistor modified was measured.

Figure 4:
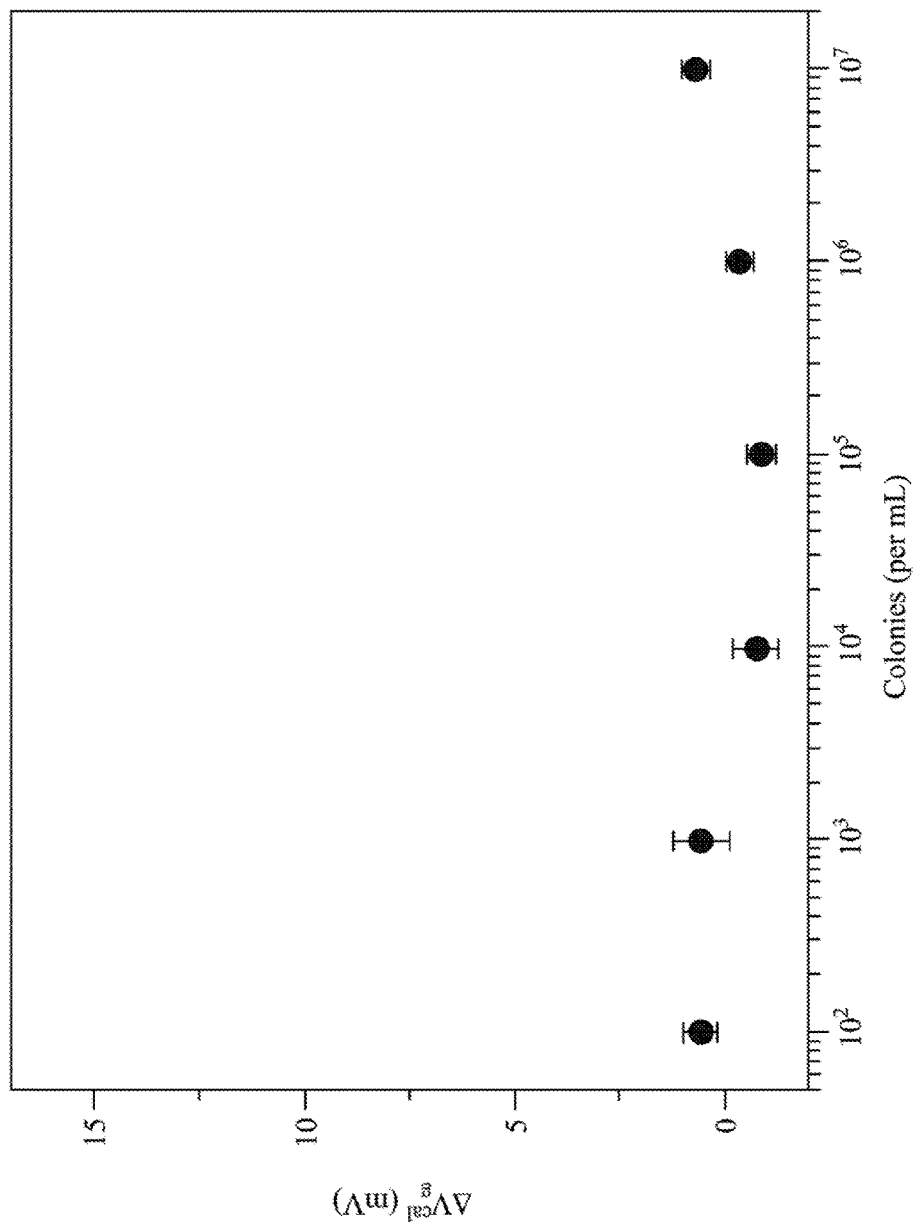
FIG. 4 is a potential difference-bacterial concentration diagram of a comparative example for a detecting experiment.

FIG. 4 is a potential difference-bacterial concentration diagram of a comparative example for a detecting experiment, which the bacterial concentration is represented by the number of colonies per mL of the broth. As shown in FIG. 4, the potential difference of the comparative example did not change accordingly with the increase of the bacterial concentration. This result suggests that the amino acid sequence in the biological sensing device of the present embodiment does not react with *Streptococcus mutans*. Although the surface of *Streptococcus mutans* also includes UlaG protein, the UlaG protein on the surface of *Streptococcus mutans* does not express. Therefore, *Streptococcus titans* is not recognized by and bound to the amino acid sequence of the biological sensing device of the present invention.

According to the results shown in FIGS. 3 and 4, the amino acid sequence 310 of the biological sensing device 300 can effectively separate and detect *Streptococcus pneumoniae* (i.e., biomolecule 400) with expressed UlaG protein 410, and does not react with *Streptococcus mutans* with unexpressed UlaG protein. The potential difference caused by the bonding of the amino acid sequence 310 and the UlaG protein 410 can be used rapid detection of *Streptococcus pneumoniae* (i.e., biomolecule 400). The biological sensing device of the repent invention uses the amino acid sequence that has high binding affinity to the UlaG protein so as to detect *Streptococcus pneumoniae* expressed with the UlaG protein on its surface. Therefore, the biological sensing device of the present invention can inexpensively and quickly detect and interpret *Streptococcus pneumoniae*, and can be used as various detecting platforms for *Streptococcus pneumoniae*.

Given the above, the biological sensing device and the method for separating the biomolecule of the present invention utilize the high affinity between the amino acid sequence and the UlaG protein to screen the biomolecule that is labeled with the UlaG protein. The biological sensing device and the method for separating the biomolecule of the present invention can be combined with various existing detecting methods, such as fluorescent dye, quartz microbalance, and field effect transistor, to create a novel detecting platform. The biological sensing device and the method for separating the biomolecule of the present invention do not need to use polyclonal antibodies with high uncertainty or monoclonal antibodies with high cost, and have advantages of being rapid, accurate, low cost, etc, which can be used to establish a biological sensing system with high sensitivity and selectivity in clinical detection.

Although the present invention has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. A method for separating a biomolecule, comprising:
providing a sample, the sample comprising a biomolecule having L-ascorbate-6-phosphate lactonase;
contacting the sample with an amino acid sequence of SEQ ID NO: 1 or SEQ ID NO: 2;
binding the amino acid sequence with the L-ascorbate-6-phosphate lactonase, wherein SEQ ID NO: 1 or SEQ ID NO: 2 has physical contact with the L-ascorbate-6-phosphate lactonase; and
removing a portion of the sample not bound with the amino acid sequence to separate the biomolecule from the sample.

2. The method of claim 1, further comprising modifying the L-ascorbate-6-phosphate lactonase onto the biomolecule.

3. The method of claim 1, further comprising modifying the sample onto a substrate.

4. The method of claim 1, further comprising connecting the amino acid sequence to a signal-generating unit.

* * * * *

SEQUENCE LISTING

```
<160> NUMBER OF SEQ ID NOS: 2

<210> SEQ ID NO 1
<211> LENGTH: 7
<212> TYPE: PRT
<213> ORGANISM: Artificial sequence
<220> FEATURE:
<223> OTHER INFORMATION: amino acid sequence bound to UlaG protein

<400> SEQUENCE: 1

Glu Asn Ile Met Pro Val Leu
 1               5

<210> SEQ ID NO 2
<211> LENGTH: 7
<212> TYPE: PRT
<213> ORGANISM: Artificial sequence
<220> FEATURE:
<223> OTHER INFORMATION: amino acid sequence bound to UlaG protein

<400> SEQUENCE: 2

Glu Arg Ile Met Pro Val Leu
 1               5
```